United States Patent
Murphy et al.

(10) Patent No.: US 6,488,919 B1
(45) Date of Patent: Dec. 3, 2002

(54) SEMI-SOLID LOW RESIDUE WATER-CONTAINING ANTIPERSPIRANT COMPOSITION

(75) Inventors: C. Shawn Murphy, Cincinnati, OH (US); Kristin Ann Boyle, Corona del Mar, CA (US)

(73) Assignee: The Andrew Jergens Company, Cincinnati, OH (US)

( * ) Notice: Subject to any disclaimer, the term of this patent is extended or adjusted under 35 U.S.C. 154(b) by 0 days.

(21) Appl. No.: 10/097,964

(22) Filed: Mar. 14, 2002

(51) Int. Cl.$^7$ .............................. A61K 7/32; A61K 7/34; A61K 7/36; A61K 7/38; A61K 7/00; A61K 3/74

(52) U.S. Cl. .............................. 424/65; 424/66; 424/67; 424/68; 424/78.02; 424/78.8; 424/400; 424/401; 424/DIG. 15

(58) Field of Search ................................ 424/65, 78.02, 424/78.08, 400, 401, 66, 67, 68, DIG. 5

(56) References Cited

U.S. PATENT DOCUMENTS

| | | |
|---|---|---|
| 4,526,780 A | 7/1985 | Marschner et al. |
| 4,725,432 A | 2/1988 | May |
| 5,354,553 A | 10/1994 | Greczyn et al. |
| 5,833,964 A | 11/1998 | Linn et al. |
| 5,916,546 A | 6/1999 | Sawin et al. |
| 5,919,437 A | 7/1999 | Lee et al. |
| 5,972,319 A | 10/1999 | Linn et al. |
| 5,997,850 A | 12/1999 | Tang et al. |

*Primary Examiner*—Shelley A. Dodson
(74) *Attorney, Agent, or Firm*—Frost Brown Todd LLC

(57) ABSTRACT

Semi-solid antiperspirant compositions are disclosed. These compositions do not leave a significant white residue on the skin of the user and exhibit good skin feel when applied. In addition, the compositions allow for the incorporation of free water into the formulation without deactivating the antiperspirant active. This is particularly useful in the incorporation of solutions of natural botanical components into the antiperspirant composition. The semi-solid antiperspirant compositions of the present invention comprise from about 5% to about 35% of a particulate antiperspirant active; from about 10% to about 60% of a volatile solvent; from about 2% to about 15% of a thickening agent; from about 1% to about 10% of an ester wax; and from about 0.5% to about 10% water.

17 Claims, No Drawings

SEMI-SOLID LOW RESIDUE WATER-CONTAINING ANTIPERSPIRANT COMPOSITION

TECHNICAL FIELD

The present invention relates to a topical composition which, when applied to the human body, provides an antiperspirant benefit to the user. Particularly, the present invention relates to an antiperspirant composition in semi-solid form, such as a soft solid, gel or cream.

BACKGROUND OF THE INVENTION

Antiperspirant and deodorant products are widely used throughout the world today. Their primary benefit, of course, is their ability to suppress perspiration and/or odors on the body of the user. Since such compositions are generally applied topically to the skin, it is important, when formulating antiperspirant compositions, to make sure that they do not irritate the skin, that they do not leave an unsightly residue on the skin or clothes (i.e., that they are "non-whitening") and that they provide good skin feel to the user. A product which leaves a white residue on the skin or clothes, or which feels cold, sticky or slimy when applied to the skin may be purchased once, but will not generally be re-purchased by the consumer. In the past, formulating a non-whitening product has been accomplished using mechanical processing means for the composition or through the use of butylene glycol in the composition. The utility of mechanical processing is limited since high shear mixing can only achieve a certain level of non-whitening on the skin. While butylene glycol is effective as a non-whitening agent, it tends to be sticky and tacky to the touch and, therefore, tends to result in undesirable skin feel properties for the compositions which incorporate it.

In the past, water or water-based extracts or additives have not been incorporated into antiperspirant compositions because they interact negatively with the antiperspirant active. Thus, when water is added to a conventional antiperspirant composition, the water and active form a precipitate which settles out of the anhydrous system, causing both cosmetic and efficacy problems.

The present invention permits the use of water in an antiperspirant semi-solid composition, as well as allowing the formulation of these compositions such that they are non-whitening on the skin while at the same time having good skin feel, through the incorporation of an ester wax material.

U.S. Pat. No. 4,937,069, Shin, issued Jun. 26, 1990, describes a substantially anhydrous semi-solid antiperspirant composition consisting essentially of 1–50% of an antiperspirant active powder; 2–6% of a fumed silica thickening/suspending agent (such as Cab-O-Sil®); 2–6% of a thickening/solid emollient (such as stearyl alcohol or hydrogenated castor oil); 2–15% of a nonvolatile liquid emollient/plasticizer (such as PEG-100 stearate, glyceryl stearate or PEG-20 sorbitan isostearate); and 30–70% of a volatile emollient (such as cyclomethicone). Water or water-based components are not incorporated into the disclosed compositions.

U.S. Pat. No. 5,756,082, Cashin, et al., issued May 26, 1998, relates to cosmetic sticks (which are defined to include soft solid antiperspirant compositions) comprising 24–60% of a volatile silicone (such as cyclomethicone), 3–25% of a wax (such as stearyl alcohol or hydrogenated castor oil), and 10–40% of a gel component which comprises mineral oil or (butylene or propylene)/ethylene/styrene copolymers. Disclosed compositions include very low levels of PEG-25 propylene glycol stearate (0.15%) and water (0.5%).

International Patent Application WO 99/51192, Colgate-Palmolive Company, published Oct. 14, 1999, relates to low residue cosmetic compositions (for example, antiperspirant compositions) which include an active ingredient, a silicone gel material comprising an elastomer composition, and at least one surfactant having an HLB value of from 8–16. Emollients such as PEG-25, PEG stearate, glyceryl stearate, and PEG-100 stearate may be included in the disclosed compositions. The compositions are taught to exhibit reduced or eliminated film formation when applied to the skin, together with increased availability of the active ingredient.

SUMMARY OF THE INVENTION

The present invention relates to semi-solid antiperspirant compositions which comprise:
(a) from about 5% to about 35% of a particulate antiperspirant active;
(b) from about 10% to about 60% of a volatile solvent, such as cyclomethicone D5 (decamethylcyclopentasiloxane);
(c) from about 2% to about 15% of a thickening agent, for example a solid emollient material such as stearyl alcohol or hydrogenated castor oil;
(d) from about 1% to about 10% of an ester wax, such as ester waxes having a total carbon content of from about 12 to about 40 carbons (examples include glyceryl stearate and sorbitan isostearate); and
(e) from about 0.5% to about 10% of water or a water-containing component, such as a water-based botanical extract (e.g., ginger extract).

These compositions not only provide effective antiperspirant performance to the user in an aesthetically acceptable semi-solid formulation (such as a soft solid composition, a gel or a cream), but also minimize the amount of skin whitening and provide acceptable skin feel to the user. In addition, from a formulational point of view, the antiperspirant compositions of the present invention allow for the incorporation of water or water-based components (such as botanical extracts) into an otherwise anhydrous antiperspirant system, without resulting in the deactivation of the antiperspirant active material.

All percentages and ratios given herein are "by weight" unless otherwise specified.

All patents and publications noted in this application are incorporated herein by reference.

DETAILED DESCRIPTION OF THE INVENTION

The semi-solid antiperspirant compositions of the present invention include a particulate antiperspirant active, a volatile solvent, a thickening agent component, an ester wax and water, and may optionally contain additional components conventionally found in topical antiperspirant compositions. Each of those components, as well as the methods of making and using the compositions of the present invention, will be discussed in detail below.

As used herein, the term "semi-solid composition" is intended to encompass compositions which typically have a penetration force value of at least about 100 grams, as measured at 27° C., 15% relative humidity, using conventional devices, for example a TA-XT2 texture analyzer, manufactured by Text Technology Corp., Scarsdale, N.Y. The penetration force value is not so high as to define a solid composition. Examples of semi-solid compositions include soft solid sticks, gels, and creams. The viscosities of the semi-solid compositions lie between those of liquids (on the low end) and solid sticks (on the high end).

The present composition contains from about 5% to about 35%, preferably from about 15% to about 26%, by weight of a particulate antiperspirant material. These weight percentages are calculated on an anhydrous metal salt basis (exclusive of glycine, the salts of glycine, or other complexing agents). The particulate antiperspirant material preferably has a particle size ranging about 1 to about 100 microns, more preferably from about 1 to about 50 microns. They may be impalpable or microspherical in form and, preferably, have a high bulk density (for example, greater than about 0.7 g/cm$^3$). Any particulate antiperspirant materials known in the art may be used in the present invention. Such materials include, for example, many aluminum or zirconium astringent salts or complexes. Examples of useful antiperspirant materials are described in U.S. Pat. No. 6,287,544, Franklin, et al., issued Sep. 11, 2001; U.S. Pat. No. 6,261,543, Fletcher, et al., issued Jul. 17, 2001; and U.S. Pat. No. 6,187,301, Scavone, et al., issued Feb. 13, 2001; all incorporated herein by reference.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692, Gilman, issued Jun. 3, 1975, and U.S. Pat. No. 3,904,741, Jones and Rubino, issued Sep. 9, 1975, incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2−nz is greater than or equal to 0, and B may be selected from the group consisting of halides, nitrate, sulfamate, sulfate, and mixtures thereof. Although only zirconium compounds are exemplified in this context, it will be understood that other Group IV B metal compounds, including hafnium, could be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example, U.S. Pat. No. 3,792,068, Luedders et al., issued Feb. 12, 1974, incorporated herein by reference, discloses complexes of aluminum, zirconium and amino acids such as glycines. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by:
(A) co-dissolving in water
(1) one part $Al_2(OH)_{6-m}Q_m$, wherein Q is an anion selected from the group consisting of chloride, bromide and iodide, and m is a number from about 0.8 to about 2.0;
(2) x parts $ZrO(OH)_{2-a}Q_a \cdot nH_2O$, where Q is chloride, bromide or iodide; where a is from about 1 to about 2; where n is from about 1 to about 8; and where x has a value of from about 0.16 to about 1.2;
(3) p parts neutral amino acid selected from the group consisting of glycine, dl-tryptophane, dl-β-phenylalanine, dl-valine, dl-methionine and β-alanine, and where p has a value of from about 0.06 to about 0.53;
(B) co-drying the resultant mixture to a friable solid; and
(C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl \cdot 2H_2O$. Preferred zirconium compounds for preparation of such ZAG-type complexes are zirconyl hydroxychloride having the empirical formula $ZrO(OH)Cl \cdot 3H_2O$ and the zirconyl hydroxyhalides of the empirical formula $ZrO(OH)_{2-a}Cl_2 \cdot nH_2O$ wherein a is from about 1.5 to about 1.87, and n is from about 1 to about 7. The preferred amino acid for preparing such ZAG-type complexes is glycine of the formula $CH_2(HN_2)COOH$. Salts of such amino acids can also be employed in the antiperspirant complexes. See U.S. Pat. No. 4,017,599, Rubino, issued Apr. 12, 1977, incorporated herein by reference.

A wide variety of other types of antiperspirant complexes are also known in the art. For example, U.S. Pat. No. 3,903,258, Siegal, issued Sep. 2, 1975, discloses a zirconium aluminum complex prepared by reacting zirconyl chloride with aluminum hydroxide and aluminum chlorhydroxide. U.S. Pat. No. 3,979,510, Rubino, issued Sep. 7, 1976, discloses an antiperspirant complex formed from certain aluminum compounds, certain zirconium compounds, and certain complex aluminum buffers. U.S. Pat. No. 3,981,896, issued Sep. 21, 1976, discloses an antiperspirant complex prepared from an aluminum polyol compound, a zirconium compound and an organic buffer. U.S. Pat. No. 3,970,748, Mecca, issued Jul. 20, 1976, discloses an aluminum chlorhydroxy glycinate complex of the approximate general formula $[Al_2(OH)_4Cl][H_2CNH_2—COOH]$. All of these patents are incorporated herein by reference.

Of all the above types of antiperspirant actives, preferred compounds include the 5/6 basic aluminum salts of the empirical formula $Al_2(OH)_5Cl \cdot 2H_2O$; mixtures of $AlCl_3 \cdot 6H_2O$ and $Al_2(OH)_5Cl \cdot 2H_2O$ with aluminum chloride to aluminum hydroxychloride weight ratios of up to about 0.5; ZAG-type complexes wherein the zirconium salt is $ZrO(OH)Cl \cdot 3H_2O$, the aluminum salt is $Al_2(OH)_5Cl \cdot 2H_2O$ or the aforementioned mixtures of $AlCl_3 \cdot 6H_2O$ and $Al_2(OH)_5Cl \cdot 2H_2O$ wherein the total metal to chloride molar ratio in the complex is less than about 1.25, the Al:Zr molar ratio is about 3.3, and the amino acid is glycine; and ZAG-type complexes wherein the zirconium salt is $ZrO(OH)_{2-a}Cl_a \cdot nH_2O$ wherein a is from about 1.5 to about 1.87 and n is from about 1 to about 7, the aluminum salt is $Al_2(OH)_5Cl \cdot 2H_2O$ and the amino acid is glycine.

Preferred particulate antiperspirant materials include inorganic or organic salts of aluminum, zirconium or zinc, as well as mixtures of those materials. Aluminum chlorhydrate (ACH) actives and aluminum zirconium tetrachlorohydrex glycine complex are particularly preferred antiperspirant actives for use in the present invention, with the aluminum zirconium tetrachlorohydrex glycine complex being particularly preferred.

Volatile hydrocarbon solvents (such as dodecene) and volatile silicone solvents are well known for use in cosmetic and deodorant sticks and may be used herein. Volatile silicones known for use in deodorant sticks are preferred for use in the present invention. The volatile silicone material is preferably either a cyclic or a linear polydimethylsiloxane and is present at a level of from about 10% to about 60%, preferably from about 20% to about 50%, of the composition.

The cyclic polydimethylsiloxanes preferably include from about 3 to about 7 silicon atoms, more preferably from about 4 to about 5 silicon atoms. The general formula for such siloxanes is wherein n is from about 3 to about 7. The linear polydimethylsiloxanes contain from about 3 to about 9 silicon atoms and have the general formula $(CH_3)_3Si-O[Si(CH_3)_2-O]n-Si(CH_3)_3$, wherein n is from about 1 to about 7.

Silicones of the above type are commercially available, for example, from Dow Corning Corporation (Dow Corning 344, 345 and 200 fluids), Union Carbide (Silicone 7207 and Silicone 7158), and Stauffer Chemical (SWS-03314), as well as from General Electric Specialty Chemicals.

The linear volatile silicone materials generally have viscosities of less than about 5 centistokes at 25° C., while the cyclic materials have viscosities less than about 10 centistokes. "Volatile" means that the material has a measurable vapor pressure. A description of volatile silicones is found in Todd and Byers, "Volatile Silicone Fluids for Cosmetics", Cosmetics and Toiletries, 91:27–32 (1976), incorporated herein by reference.

Cyclic polydimethylsiloxanes, and particularly cyclomethicone D-5 (decamethylcyclopentasiloxane) and D-7 (tetradecamethylcycloheptasiloxane), are preferred for use in the compositions of the present invention.

The thickening agent component is present in the compositions of the present invention at from about 2% to about 15%, preferably from about 2% to about 10%, of the total composition. Thickening agent materials must be appropriate for topical administration, compatible with other ingredients in the composition, and have composition thickening properties. Conventional topical thickening agents for human use, such as silica and clays, may be used in the compositions herein. However, preferred thickening agents are solid emollient materials which have a melting point of at least about 40° C.; these materials are generally selected from high melting point and low melting point waxes, and mixtures of those materials, although other well-known materials may be used. Examples of these preferred solid emollient materials useful in the present invention include $C_{14}$–$C_{40}$ fatty alcohols, polyethylenes, alkyl ($C_{18}$–$C_{45}$) methylsiloxanes, jojoba ester waxes, hydrogenated vegetable oils, and mixtures thereof. High melting point waxes (66–101° C.) include such materials as beeswax, montan, ozokerite, ceresin, paraffin, hydrogenated castor oil, and $C_{26}$–$C_{40}$ linear alcohols. Low melting point waxes (40–65° C.) include such materials as $C_{14}$–$C_{25}$ fatty alcohols, fatty esters, fatty amides, particularly stearyl alcohol, cetyl alcohol, stearic acid, and polydimethylsiloxanyl beeswax. $C_{16}$–$C_{22}$ fatty acids and fatty alcohols are preferred low melting point waxes. Preferred thickening agent/solid emollient materials include stearyl alcohol, hydrogenated castor oil, and mixtures of stearyl alcohol and hydrogenated castor oil. Other examples include mineral oil and petrolatum.

The compositions of the present invention also include from about 1% to about 10% of a hydrophobic organic ester wax material. Although the identity of the specific ester or combination of esters is not especially critical, it has been found that suitable esters include at least about 10 carbon atoms, and preferably the ester includes from about 12 to about 40 carbon atoms. For example, suitable esters encompass those comprising an alcohol or polyol including from about 8 to about 20 carbon atoms and a carboxylic acid including from about 2 to about 20 carbon atoms, or conversely an alcohol or polyol including from about 2 to about 20 carbon atoms with a carboxylic acid including from about 8 to about 20 carbon atoms. Examples of suitable esters include glycerol or sorbitol esters of $C_{14}$–$C_{30}$ fatty acids, with particularly preferred esters being glyceryl stearate, sorbitan isostearate, and mixtures of those materials.

Although semi-solid antiperspirant compositions typically are anhydrous (i.e., they do not contain free water), since the water tends to negatively interact with the antiperspirant active unless used in a carefully designed formulation, the compositions of the present invention contain from about 0.5% to about 10%, preferably from about 1% to about 8%, more preferably from about 3% to about 8%, of water. The presence of the other components in the present compositions, particularly the ester waxes, allows the introduction of water without deactivating the antiperspirant active material. As used herein, the term "water" is intended to encompass both free water itself, and water used as a solvent in a water-based component, such as a botanical extract. The water will typically be added to the composition in the form of a solvent for a water-soluble component, although it may be added as free water as well. Examples of a material which may be added to the composition of the present invention as a water solution include botanical or natural plant extracts, such as ginger extract, which may be added to achieve aesthetic or skin treatment benefits.

Examples of botanical extracts which may be included in the compositions of the present invention as aqueous solutions include ginger rhizome, almond, birch, clove, rose hip, white birch, gambi, burnet, hiba, willow herb, Phellodendron Amurense, Coptis Chinesis, clove oil extract, tea tree oil, olive leaf extract, rosemary extract, fennel seed, phytoplenolin, sericin, K2 glycerrizinate, capsaicin, menthol and menthyl lactate. Preferred materials include ginger extract, burnet extract, and mixtures of those materials. A particularly preferred material is ginger root extract (Zingiber Officinale), which can reduce the diameter and length of underarm hair and therefore decrease the amount of shaving required by the user.

The compositions of the present invention may also contain optional components conventionally used in antiperspirant or deodorant compositions which modify the physical characteristics of the semi-solid antiperspirant composition or components of that composition or serve as "active" component when deposited on the skin in addition to the particulate antiperspirant material. Examples of such additional actives include bacteriostats and fungistats. Optional components useful herein are described in the following documents, all incorporated herein by reference: U.S. Pat. No. 4,049,792, Elsnau, issued Sep. 20, 1977; Canadian Patent 1,164,347, Beckmeyer et al., issued Mar. 27, 1984; European Patent Specification 117,070, May, published Aug. 29, 1984; and Geria, "Formulation of Stick Antiperspirants and Deodorants", Cosmetics and Toiletries, 99:55–60 (1984); all incorporated herein by reference.

The specific nonactive components that may be used in the present invention will depend upon the characteristics desired for the particular semi-solid antiperspirant compositions. These components are used at their art-established levels to achieve their art-established benefits. Such components include, for example, emollients, colorants, perfumes, emulsifiers, surfactants, preservatives, and skin feel enhancers. Although the present compositions may also contain fillers and particulate materials (such as talc, starch and silica (fumed and nonfumed, as well as mixtures thereof)) in addition to the antiperspirant active described above, such particulates may adversely affect the perceived low residue benefits of the present invention and, therefore, they should be used carefully with their levels appropriately minimized.

The antiperspirant compositions of the present invention may be manufactured using methods known in the art. Typical procedures are described in the examples given below.

The low residue semi-solid antiperspirant compositions of the present invention are used in a conventional manner. Specifically, the compositions may be used to prevent and/or control perspiration wetness by topically applying, one or more times a day, an effective amount of the composition to areas of the body particularly prone to perspiration (for example, the underarm or axillary area).

The following nonlimiting examples illustrate the compositions, method of making, and methods of using the present invention described in this application.

EXAMPLE 1

A semi-solid antiperspirant compositions of the present invention, having the composition given in the table below, is formulated using the procedure described. The composition is stable, provides good antiperspirant performance with good skin feel and minimized skin whitening, and effectively incorporates the water-containing botanical extract component.

Method of Manufacture:

Step 1. In a suitable stainless steel steam jacketed vessel, add the cyclomethicone and colloidal silicon dioxide. Heat to 72+/−5° C. Mix until the colloidal silicon dioxide is well dispersed.

Step 2. In a separate stainless steel steam jacketed pre-mix vessel, add the stearyl alcohol, hydrogenated castor oil, petrolatum, PEG-20 sorbitan isostearate, glyceryl stearate PEG-100 stearate, and water-containing botanical extract. Heat to 85+/−5° C. Mix until homogeneous. Add to the mixture of Step 1.

Step 3. Add the talc to the batch and mix until homogeneous.

Step 4. Add the aluminum zirconium tetrachlorohydrex-gly powder to the batch. Mix until a homogeneous semi-solid cream is formed. Mix for an additional 15 minutes and cool to room temperature.

The composition is packaged in a cream stick dispenser and is dispensed by extrusion.

Composition:

| COMPONENTS | % W/W |
| --- | --- |
| Cyclomethicone | 40.25 |
| Colloidal Silicon Dioxide | 2.25 |
| Stearyl Alcohol | 2.00 |
| Hydrogenated Castor Oil MP-80 | 3.00 |
| Petrolatum | 10.00 |
| PEG-20 Sorbitan Isostearate | 1.00 |
| Glyceryl Stearate and PEG-100 Stearate | 2.50 |
| Water-containing Botanical Extract | 8.00 |
| Talc | 7.00 |
| Aluminum Zirconium Tetrachlorohydrex Gly Powder | 24.00 |
| TOTAL | 100.00 |

EXAMPLE 2

A semi-solid antiperspirant compositions of the present invention, having the composition given in the table below, is formulated using the procedure described. The composition is stable, provides good antiperspirant performance with good skin feel and minimized skin whitening, and effectively incorporates the water-containing botanical extract component.

Method of Manufacture:

Step 1. In a suitable stainless steel steam jacketed vessel, add the cyclomethicone and dimethicone. Slowly mix and heat to 72+/−5° C.

Step 2. Add the colloidal silicon dioxide to the mixture of Step 1 slowly while maintaining the temperature at 72+/−5° C.

Step 3. In a separate stainless steel steam jacketed pre-mix vessel, add the hydrogenated castor oil, PPG-9 steareth-3, glyceryl stearate, PEG-100 stearate, and water-containing botanical extract. Heat to 85+/−° C. Mix until homogeneous. Add to the mixture of Steps 1 and 2.

Step 4. Add the aluminum zirconium tetrachlorohydrex-gly powder to the batch. Mix until a homogeneous semi-solid cream is formed. Mix for an additional 15 minutes and cool to room temperature.

Step 5. Add the talc to the batch and mix until homogeneous.

The composition is packaged in a cream stick dispenser and is dispensed by extrusion.

Composition:

| COMPONENTS | % W/W |
| --- | --- |
| Cyclomethicone | 50.00 |
| Colloidal Silicon Dioxide | 4.00 |
| Hydrogenated Castor Oil MP-80 | 3.00 |
| Dimethicone (100cs) | 2.00 |
| PPG-9 Steareth-3 | 3.75 |
| Glyceryl Stearate and PEG-100 Stearate | 1.25 |
| Water-containing Botanical Extract | 5.00 |
| Talc | 7.00 |
| Aluminum Zirconium Tetrachlorohydrex Gly Powder | 24.00 |
| TOTAL | 100.00 |

EXAMPLE 3

A semi-solid antiperspirant compositions of the present invention, having the composition given in the table below, is formulated using the procedure described. The composition is stable, provides good antiperspirant performance with good skin feel and minimized skin whitening, and effectively incorporates the water-containing botanical extract component.

Method of Manufacture:

Step 1. In a suitable stainless steel steam jacketed vessel, add the cyclomethicone, dimethicone, PPG-14 butyl ether, fluid AP, PPG-3-isosteareth-9, PPG-5-cetheth-20 and water-containing botanical extract. Melt while slowly mixing by heating to 72+/−5° C., until homogeneous.

Step 2. Add the colloidal silicon dioxide to the mixture of Step 1 slowly while maintaining the temperature at 72+/−5° C.

Step 3. Add the corn starch to the batch and mix until homogeneous.

Step 4. Add the aluminum zirconium tetrachlorohydrex-gly powder to the batch. Mix until a homogeneous semi-solid cream is formed. Mix for an additional 15 minutes and cool to room temperature.

The composition is packaged in a cream stick dispenser and is dispensed by extrusion.

Composition:

| COMPONENTS | % W/W |
|---|---|
| Cyclomethicone | 46.75 |
| Dimethicone (100cs) | 2.00 |
| Colloidal Silicon Dioxide | 4.50 |
| PPG-14 Butyl Ether | 2.00 |
| Fluid AP | 3.00 |
| PPG-3-Isosteareth-9 | 3.75 |
| PPG-5-Cetheth-20 | 2.00 |
| Water-containing Botanical Extract | 8.00 |
| Corn Starch | 4.00 |
| Aluminum Zirconium Tetrachlorohydrex Gly Powder | 24.00 |
| TOTAL | 100.00 |

EXAMPLE 4

A semi-solid antiperspirant compositions of the present invention, having the composition given in the table below, is formulated using the procedure described. The composition is stable, provides good antiperspirant performance with good skin feel and minimized skin whitening, and effectively incorporates the water-containing botanical extract component.

Method of Manufacture:

Step 1. (PRE-MIX 1) In a separate stainless steel steam jacketed pre-mix vessel, add the Bentone 38 VCG powder and one-third of the total amount of cyclomethicone. Using a homomixer, mix until homogeneous. Add the propylene carbonate.

Step 2. In a suitable stainless steel steam jacketed mixing vessel, add the cyclomethicone, fluid AP and colloidal silicon dioxide. Heat to 72+/−5° C. Mix until the colloidal silicon dioxide is well dispersed.

Step 3. Add the Step 1 pre-mix to the mixture of Step 2. Continue heating and mixing to 72+/−5° C.

Step 4. (PRE-MIX 2) In a separate stainless steel steam jacketed pre-mix vessel, add the hydrogenated castor oil, PEG-20 sorbitan isostearate, glycerin stearate, PEG-100 stearate and water-containing botanical extract. Heat to 85+/−5° C. Mix until homogeneous. Add to the mixture of Step 3.

Step 5. Add the aluminum zirconium tetrachlorohydrex-gly powder to the batch. Mix until a homogeneous semi-solid cream is formed. Mix for an additional 15 minutes and cool to room temperature.

Step 5. Add the talc to the batch and mix until homogeneous.

The composition is packaged in a cream stick dispenser and is dispensed by extrusion.

Composition:

| COMPONENTS | % W/W |
|---|---|
| Cyclomethicone | 46.25 |
| Colloidal Silicon Dioxide | 2.25 |
| Fluid AP | 2.00 |
| Hydrogenated Castor Oil MP-80 | 3.00 |
| Bentone 38 VCG | 3.25 |
| Propylene Carbonate | 0.75 |
| PEG-20 Sorbitan Isostearate | 1.00 |
| Glyceryl Stearate and PEG-100 Stearate | 2.50 |
| Water-containing Botanical Extract | 8.00 |
| Talc | 7.00 |
| Aluminum Zirconium Tetrachlorohydrex Gly Powder | 24.00 |
| TOTAL | 100.00 |

What is claimed is:

1. An semi-solid antiperspirant composition comprising:
   (a) from about 5% to about 35% of a particulate antiperspirant active;
   (b) from about 10% to about 60% of a volatile solvent;
   (c) from about 2% to about 15% of a thickening agent;
   (d) from about 1% to about 10% of an ester wax; and
   (e) from 0.5% to about 10% water.

2. The antiperspirant composition according to claim 1 wherein the antiperspirant active comprises materials selected from organic or inorganic salts of aluminum, zirconium, zinc, and mixtures thereof.

3. The antiperspirant composition according to claim 2 wherein the volatile solvent is selected from cyclic polydimethylsiloxanes containing from about 3 to about 7 silicon atoms, linear polydimethylsiloxanes containing from about 3 to about 9 silicon atoms, and mixtures of those materials.

4. The antiperspirant composition according to claim 3 wherein the thickening agent is a solid emollient material selected from $C_{14}$–$C_{40}$ fatty alcohols, polyethylene, $C_{18}$–$C_{45}$ alkyl methyl siloxanes, jojoba ester waxes, hydrogenated vegetable oils, and mixtures thereof.

5. The antiperspirant composition according to claim 4 wherein the ester wax is a hydrophobic ester containing from about 12 to about 40 carbon atoms.

6. The antiperspirant composition according to claim 5 wherein the ester wax is a selected from glycerol or sorbitol esters of $C_{14}$–$C_{30}$ fatty acids.

7. The antiperspirant composition according to claim 5 wherein the volatile solvent is a cyclic polydimethylsiloxane containing from about 3 to about 7 silicon atoms.

8. The antiperspirant composition according to claim 6 wherein the ester wax is selected from glyceryl stearate, sorbitan isostearate, and mixtures thereof.

9. The antiperspirant composition according to claim 8 wherein the thickening agent is selected from stearyl alcohol, hydrogenated castor oil, and mixtures thereof.

10. The antiperspirant composition according to claim 4 wherein the thickening agent is selected from stearyl alcohol, hydrogenated castor oil, and mixtures thereof.

11. The antiperspirant composition according to claim 4 wherein the ester wax is selected from glyceryl stearate, sorbitan isostearate, and mixtures thereof.

12. The antiperspirant composition according to claim 10 which contains from about 1% to about 8% water.

13. The antiperspirant composition according to claim 12 which contains from about 15% to about 26% of the antiperspirant active; from about 20% to about 50% of the volatile solvent; and from about 2% to about 10% of the thickening agent.

14. The antiperspirant composition according to claim 13 wherein at least a portion of the water component is present in the form of solvent for a water-soluble component.

15. The antiperspirant composition according to claim 14 wherein at least a portion of the water is present in the form of the water solvent for a solution of ginger extract.

16. The antiperspirant composition according to claim 9 wherein at least a portion of the water component is present in the form of a solvent for a water-soluble component.

17. The antiperspirant composition according to claim 16 wherein at least a portion of the water is present in the form of the water solvent for a solution of ginger extract.

* * * * *